US011648259B2

(12) United States Patent
Marquardt et al.

(10) Patent No.: US 11,648,259 B2
(45) Date of Patent: May 16, 2023

(54) APTAMERS FOR MYCOTOXIN DETOXIFICATION

(71) Applicant: MYCOTOX SOLUTIONS INC., Winnipeg (CA)

(72) Inventors: Ronald R. Marquardt, Winnipeg (CA); Srinivasa Madhyastha, Winnipeg (CA)

(73) Assignee: Mycotox Solutions Inc., Manitoba (CA)

( * ) Notice: Subject to any disclaimer, the term of this patent is extended or adjusted under 35 U.S.C. 154(b) by 752 days.

(21) Appl. No.: 15/773,044

(22) PCT Filed: Sep. 14, 2016

(86) PCT No.: PCT/CA2016/051083
§ 371 (c)(1),
(2) Date: May 2, 2018

(87) PCT Pub. No.: WO2017/075696
PCT Pub. Date: May 11, 2017

(65) Prior Publication Data

US 2018/0325936 A1 Nov. 15, 2018

Related U.S. Application Data

(60) Provisional application No. 62/249,621, filed on Nov. 2, 2015.

(51) Int. Cl.

| | |
|---|---|
| ***C12N 15/115*** | (2010.01) |
| ***A61K 31/7088*** | (2006.01) |
| ***A61K 39/395*** | (2006.01) |
| ***A61K 33/06*** | (2006.01) |
| ***A23K 20/153*** | (2016.01) |
| ***A23L 33/13*** | (2016.01) |
| ***A23L 33/17*** | (2016.01) |
| ***A23K 10/18*** | (2016.01) |
| ***A23K 20/174*** | (2016.01) |
| ***A23K 20/179*** | (2016.01) |
| ***A23K 20/111*** | (2016.01) |
| ***A23K 20/132*** | (2016.01) |
| ***A23K 20/147*** | (2016.01) |
| ***A23K 20/163*** | (2016.01) |
| ***A23K 20/189*** | (2016.01) |
| ***A23K 20/28*** | (2016.01) |
| ***A23K 20/20*** | (2016.01) |
| ***A23K 50/20*** | (2016.01) |
| ***A23K 50/10*** | (2016.01) |
| ***A23K 50/75*** | (2016.01) |
| ***A23K 50/30*** | (2016.01) |
| ***A23K 50/40*** | (2016.01) |
| ***C07K 16/14*** | (2006.01) |
| ***A23K 20/142*** | (2016.01) |

(Continued)

(52) U.S. Cl.
CPC .......... *A61K 31/7088* (2013.01); *A23K 10/16* (2016.05); *A23K 10/18* (2016.05); *A23K 20/111* (2016.05); *A23K 20/132* (2016.05); *A23K 20/142* (2016.05); *A23K 20/147* (2016.05); *A23K 20/153* (2016.05); *A23K 20/163* (2016.05); *A23K 20/174* (2016.05); *A23K 20/179* (2016.05); *A23K 20/189* (2016.05); *A23K 20/28* (2016.05); *A23K 20/30* (2016.05); *A23K 50/10* (2016.05); *A23K 50/20* (2016.05); *A23K 50/30* (2016.05); *A23K 50/40* (2016.05); *A23K 50/75* (2016.05); *A23L 33/10* (2016.08); *A23L 33/13* (2016.08); *A23L 33/17* (2016.08); *A61K 33/06* (2013.01); *A61K 39/395* (2013.01); *A61K 45/06* (2013.01); *A61P 31/10* (2018.01); *C07K 16/14* (2013.01); *C12N 15/115* (2013.01); *C12N 2310/16* (2013.01)

(58) Field of Classification Search
CPC .......................... C12N 15/115; C12N 2310/16
See application file for complete search history.

(56) References Cited

U.S. PATENT DOCUMENTS

2007/0071795 A1* 3/2007 Pradip .................. A23K 20/195 424/442
2012/0225494 A1 9/2012 Le
2017/0121715 A1* 5/2017 Wang ...................... C12Q 1/68

FOREIGN PATENT DOCUMENTS

WO 2011/020198 2/2011

OTHER PUBLICATIONS

Ma et al., Selection, identification, and application of Aflatoxin B1 aptamer, European Food Research and Technology, vol. 238, pp. 919-925. (Year: 2014).*

(Continued)

*Primary Examiner* — Dana H Shin

(57) ABSTRACT

Mycotoxin-deactivating aptamers, especially DNA aptamers, bind to mycotoxins in feed and feed ingredients resulting in the reduction or elimination of toxic and carcinogenic effects of mycotoxins. The invention also discloses a composition comprising a mycotoxin-deactivating aptamer, a binding agent, a biotransforming agent and an antioxidant for detoxifying mycotoxins in feeds. In addition, the invention teaches the methods of preparing the mycotoxin-deactivating aptamer-based composition and also the methods of using it as a feed additive. Furthermore, the invention relates to the use of the mycotoxin-deactivator/s alone, or in a composition comprising the aptamers and other mycotoxin-detoxifying agents, in feeds and feed ingredients for detoxifying the major mycotoxins such as aflatoxins, deoxynivalenol, zearalenone, fumonisins and ochratoxin A.

20 Claims, 2 Drawing Sheets

Specification includes a Sequence Listing.

(51) Int. Cl.

| | |
|---|---|
| ***A23L 33/10*** | (2016.01) |
| ***A23K 10/16*** | (2016.01) |
| ***A61P 31/10*** | (2006.01) |
| ***A61K 45/06*** | (2006.01) |

(56) References Cited

OTHER PUBLICATIONS

Devreese et al., Different methods to counteract mycotoxin production and its impact on animal health, Vlamms Diergenneskundig Tijdschrift, vol. 82, pp. 181-190. (Year: 2013).*
Imaizumi et al., Efficay of base-modification on target binding of small molecule DNA aptamers, JACS, vol. 135, pp. 9412-9419. (Year: 2013).*
Kolosova et al., Substances for reduction of the contamination of feed by mycotoxins: a review, World Mycotoxin Journal, vol. 4, pp. 225-256. (Year: 2011).*
Pierzynowska et al., Antimutagenic effects of ellagic acid, rutin and psoralen against aflatoxin B1, Journal of Animal and Feed Sciences, vol. 7, pp. 277-283. (Year: 1998).*
Karlovsky, Petr, et al., Impact of Food Processing and Detoxification Treatments on Mycotoxin Contamination, Mycotoxin Res (2016) 32:179-205.
Kaur, Harleen, et al., Aptamers in the Therapeutics and Diagnostics Pipeline, Theranostics 2018; 8(15): 4016-4032.
Davydova, Anna, et al., Aptamers Against Pathogenic Microorganisms, Crit Rev Microbiol, 2016; 42(6): 847-865.

* cited by examiner

Aflatoxin B1 (AFB1)

+

AFB1 Binding Specific Nuclease-Resistant Aptamer Sequence of

SEQ ID NO. 1:

5'- GTT GGG CAC GTG TTG TCT CTC TGT GTC TCG TGC CCT TCG CTA GGC CCA CA/3InvdT/-3'

[1]Y-Axis: % Lethality in Zebrafish; X-Axis: 4 Treatments, (i) 0.1% DMSO (Control), (ii) Aptamer Alone, (iii) AFB1 Alone, and (iv) AFB1+ Aptamer Combination

SEQUENCE LISTING

<160> NUMBER OF SEQ ID NOS: 1

<210> SEQ ID NO 1
<211> LENGTH: 51
<212> TYPE: DNA
<213> ORGANISM: Artificial
<220> FEATURE:
<221> NAME/KEY: misc_feature
<222> LOCATION: (51)..(51)
<223> OTHER INFORMATION: chemically synthesized - t is inverted dT

<400> SEQUENCE: 1
gttgggcacg tgttgtctct ctgtgtctcg tgcccttcgc taggcccaca 50
t 51

APTAMERS FOR MYCOTOXIN DETOXIFICATION

FIELD OF THE INVENTION

The present invention relates to aptamer-based compositions for mycotoxin detoxification, more specifically DNA or RNA aptamer-based compositions, and to the methods of preparing said aptamer-based compositions. The invention also relates to the use of said aptamer-based compositions as feed additives for detoxifying mycotoxins, such as aflatoxins, deoxynivalenol, zearalenone, fumonisins and ochratoxin A.

BACKGROUND OF THE INVENTION

Mycotoxins are toxic secondary metabolites produced by fungi. Only some fungi produce mycotoxins, and they are referred to as toxigenic. Mycotoxin formation may occur when the causative fungi grow on crops in the field, at harvest, in storage, or during feed processing; essentially whenever favourable conditions for their formation prevail. There are hundreds of mycotoxins known, but few have been extensively researched and even fewer have good commercially available methods for analyzing them. The primary classes of mycotoxins are Aflatoxins (B1, B2, G1, G2) of which aflatoxin B1 (AFB1) is the most prevalent, zearalenone (ZEA), trichothecenes such as deoxynivalenol (DON) and T-2 toxin (T-2), fumonisins (FUM: FB1, FB2, FB3) and ochratoxin A (OTA). The major mycotoxin-producing fugal genera are *Aspergillus, Fusarium* and *Penicillium*. Many species of these fungi produce mycotoxins in commodities, feeds and feed ingredients. Mycotoxin contamination in animal feed and human food is a worldwide problem. Rodriguez and Naehrer (Phytopathol. Mediterr. 2012; 51: 175-192) reviewed mycotoxin contamination of diverse feedstuffs samples from throughout the world for five toxins (AFB1, DON, ZEA, FUM and OTA).

Mycotoxins are toxic when contaminated feeds or feed ingredients are consumed by animals. Mycotoxicoses are diseases caused by exposure to feeds contaminated with mycotoxins (Nelson et al., 1993; Ann Rev. Phytopath. 31: 233-249). Mycotoxins exhibit a variety of biological effects in animals, which include liver and kidney toxicity, neurological, estrogenic and teratogenic effects, to name a few. Some mycotoxins such as AFB1, OTA and FB1 are carcinogenic. Additionally, the mycotoxin-contaminated feed consumption in animals can cause loss of appetite, decreased feed efficiency, feed refusal, poor weight gain, immunosuppression, and mortality. Each mycotoxin has its own particular effect, and all can be devastating. Co-contamination by multiple types of mycotoxin occurs naturally, and exerts a greater negative impact on health and productivity of livestock than contamination by individual mycotoxins.

The mycotoxin contamination of feed results in billions of dollars of economic losses to animal husbandry world-wide and in some cases in health damage to human consumers due to transfer of contamination via dairy products, eggs and meats. The estimates of the costs of mycotoxins in the US vary, with one report estimating an average $1.4 billion in damage and another estimated $5 billion per year for the US and Canada. The economic impact to the livestock industry resulting from mycotoxins in ethanol co-products (Dried Distiller's Grain and Solubles=DDGS) is estimated to be $18 million per year for fumonisins in the US swine industry. Economic losses are due to effects on livestock productivity, crop losses and the costs of regulatory programs directed toward mycotoxins.

Numerous approaches to the reduction of mycotoxin levels in agricultural commodities used as animal feed ingredients have been experimentally assessed. These include mixing and dilution with mycotoxin-free grains in order to obtain a level within regulatory guidelines, i.e. 20 ppb or less; physical methods of separation such as cleaning, density segregation and preferential fragmentation; solvent extraction; biological inactivation; thermal inactivation; and chemical inactivation with a variety of acids, aldehydes, oxidizing agents and alkalies. These approaches have been relatively unsuccessful on a commercial scale due to lack of efficacy, economic constrains of the protocols, unacceptable alteration of feed quality, or the introduction of potentially deleterious substances. There is thus a need for simple, cost effective, practical and safe processes by which animal feeds can be decontaminated or detoxified are in great demand. Another method of dealing with mycotoxin-contaminated feeds is to blend in a substance capable of binding mycotoxins, thus preventing absorption of the mycotoxins into the animal's bloodstream. These feed additives may act by reducing the bioavailability of the mycotoxins or by degrading them or transforming them into less toxic metabolites.

There are two subcategories of mycotoxin-detoxifying agents: Adsorbing Agents and Biotransforming Agents (European Food Safety Agency/EFSA Scientific Report, 2009; pp. 1-192). Adsorbing agents are also called binding agents, adsorbents and binders. Adsorbing agents reduce the exposure to mycotoxins by decreasing their bioavailability, including various mycotoxin adsorbing agents in the feed, which leads to a reduction of mycotoxin uptake as well as distribution to the blood and target organs. These adsorbents include aluminosilicates, bentonites, montmorillonites, zeolites, HSCAS (Hydrated Sodium Calcium Aluminosilicate), activated carbons, yeast cell walls, micronized fibers, and polymers (cholestyramine, polyvinylpyrrolidone). Biotransforming agents such as bacteria, yeast/fungi or enzymes degrade mycotoxins into non-toxic metabolites. Among adsorbents, the use of mineral clays as binders is common. For example, U.S. Pat. No. 5,149,549 teaches the use of a montmorillonite clay, particularly a bentonite clay, admixed with animal feeds as a mycotoxin binder. U.S. Pat. No. 5,165,946 discloses the use of a montmorillonite clay in combination with a suitable sequestrant, particularly phosphate and polyphosphate salts, as mycotoxin binders. U.S. Pat. No. 5,639,492 further refines the art, describing the use of an acid-activated calcium bentonite clay admixed with animal feeds to reduce effects of mycotoxin contamination. U.S. Pat. No. 6,045,834 proposes the combination of modified yeast cells and of inorganic minerals such as zeolite, bentonite or aluminum silicate to deactivate mycotoxins present in feeds and, thus, prevent the absorption of the mycotoxins into animal blood.

However, a drawback of mineral adsorbent such as zeolite, bentonite, and aluminosilicates is that they are usually included at concentrations of 1-2% by weight, which reduces the nutritional value of the feed. Furthermore, their activity is not specific and they adsorb only a narrow range of mycotoxins, but can reduce the adsorption of nutrients such as vitamins, minerals and amino acids. It is therefore important to find new products, which can adsorb or inactivate a broad spectrum of mycotoxins without limiting the bioavailability of nutrients and micronutrients in animals.

The objective of the present invention is to provide a novel mycotoxin deactivator, suitable for feeds, which effectively deactivates mycotoxins in a selective manner but does not have unwanted interaction with nutrients.

SUMMARY OF THE INVENTION

Figure 1:
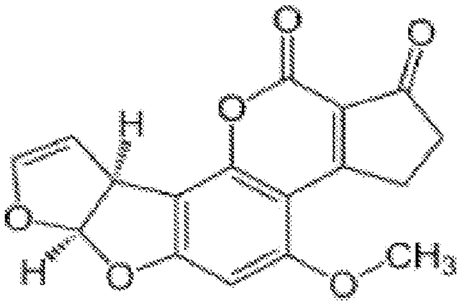
FIG. 1 shows the binding of aflatoxin B1 (AFB1) to nuclease resistant AFB1-specific aptamer.

An objective of the present invention is to provide DNA (Deoxy-Ribose Nucleic Acid) or RNA (Ribose Nucleic Acid) aptamer-based mycotoxin-deactivating compositions, which specifically deactivate mycotoxins such as AFB1, DON, ZEA, FUM and OTA, and detoxify said mycotoxins present in livestock and other animal feeds and feed ingredients.

A further objective is to provide methods of producing and using aptamer-based compositions, especially mycotoxindeactivating DNA aptamer-based composition/s for detoxifying mycotoxins present in animal feeds and feed ingredients.

Yet, a further objective is to provide a composition comprising a combination of a mycotoxin-deactivating aptamer and egg-yolk antibodies.

Another objective is to provide a composition comprising a combination of a mycotoxin-deactivating aptamer, egg-yolk antibody and one or more mycotoxin adsorbing agents selected from the group consisting of zeolites, bentonites, aluminosilicates, montmorillonites, hydrated sodium calcium aluminosilicate (HSCAS), diatomaceous earth, humic substances, yeast cell walls, micronized fibers, cholestyramine, polyvinylpyrrolidone and mineral oil.

Yet, another objective is to provide a composition comprising a combination of a mycotoxin-deactivating aptamer and one or more mycotoxin-biotransforming agents selected from the group consisting of bacteria, fungi, yeast and enzymes.

Still another objective is to provide a composition comprising a mycotoxin-deactivating aptamer and one or more adsorbing agents, and one or more biotransforming agents, and one or more antioxidants selected from the group consisting of phenolic compounds including flavonoids, vitamins, pro-vitamins, sulfur containing compounds, trace minerals, and various plant extracts.

An additional objective is to provide a composition as described above, which has an unexpected additive or synergistic binding or deactivating effect for reducing or removing mycotoxin contamination in animal feeds and feed ingredients.

Other additional objective, as described above, is to provide a composition which may be admixed with animal feeds at lower inclusion rates than that required for current commercially available mycotoxin adsorbents suitable for inclusion in animal feeds and feed ingredients. The mycotoxin-deactivating aptamers alone, or in combination with one or more adsorbing agents including mycotoxin-specific antibodies and biotransforming agents in the present invention may be added to mycotoxin-contaminated animal feed in amounts from, but not limited to, about 0.01% to 2% by weight of feed. In a preferred embodiment, the composition is added to mycotoxin-contaminated animal feed in amounts from, but not limited to, about 0.03% to 0.6% by weight of feed. In an especially preferred embodiment, the invention is added to mycotoxin-contaminated animal feed in amounts from, but not limited to, about 0.1% to 0.3% by weight of feed.

The competitive advantages and novel features of the present invention will be set forth in part in the detailed description of the invention that follows and in part will become apparent to those skilled in the art upon examination of the following or may be learned with the practice of the invention. The advantages of the invention can also be realized and obtained by means of the instrumentalities and combinations.

To achieve the foregoing and other objectives, a novel method is described for deactivating mycotoxins present in animal feeds. In particular, in a preferred embodiment, the invention provides a method and a composition for detoxifying mycotoxins present in animal feeds containing specific mycotoxin-deactivating aptamers alone or in combination with one or more adsorbing and biotransforming agents. The specific mycotoxin-deactivating aptamers production is based on SELEX (Systematic Evolution of Ligands by Exponential Enrichment) technology, which uses a library of random DNA sequences the ones with the best affinity for target mycotoxin are selected through a series of cycles with increasing stringency conditions. As aptamers are prone to nuclease degradation and sensitive to certain chemicals or physical environment, they may need to be modified either by introducing modifications into the scaffold of selected aptamers via standard solid-phase synthesis or by using modified nucleoside triphosphates directly in the selection process.

The mycotoxin-deactivating aptamers alone or in compositions, as described herein, can be fed to any animal including, but not limited to, avian, bovine, porcine, equine, ovine, caprine, canine, and feline species. When admixed with feed or fed as a supplement, the mycotoxin-deactivating aptamers alone or in compositions, with their increased mycotoxin-deactivating ability, significantly decreased absorption or uptake of the mycotoxins by the affected animals, improve animal performance and health, and reduce the incidence of mycotoxin-associated syndromes or diseases and mortality.

DETAILED DESCRIPTION OF THE INVENTION

The term "mycotoxin" means a secondary metabolite produced by fungi (mold).

The term "mycotoxicosis" means disease caused by exposure to foods and feeds contaminated with mycotoxins.

The term "binding agent" means a binding agent, which adsorbs or absorbs and/or deactivates mycotoxins present in foods and feeds, and thus reversing the adverse effects of mycotoxins.

The term "biotransforming agent" means enzyme or bacteria or yeast or fungus, which deactivates (inactivates) mycotoxins present in foods and feeds, and thus reversing the adverse effects of mycotoxins.

The term "aptamer" means a single-stranded oligonucleotide (DNA=Deoxy-ribose Nucleic Acid or RNA=Ribose Nucleic Acid) molecule, which has the ability to bind to other molecules with high affinity and specificity.

The term "oligonucleotide" nucleic acid and includes RNA or DNA sequences of more than one nucleotide in either single strand or double-stranded form. A "modified oligonucleotide" includes at least one nucleotide residue with any of: an altered internucleotide linkage(s), altered sugar(s), altered base(s), or combinations thereof.

The term "specificity" refers to the ability of an aptamer of the present invention to recognize and discriminate among competing or closely-related targets. The degree of specificity of a given aptamer is not necessarily limited to, or directly correlated with, the binding affinity of a given molecule.

The term "mycotoxin-deactivator" means an aptamer or an aptamer in a composition inactivates the activity of mycotoxin or detoxifies mycotoxin when it binds to mycotoxin.

The term "animal" includes all animals, including human beings. Examples of animals are cattle, (including but not limited to cows and calves); mono-gastric animals, e.g., pigs or swine (including, but not limited to, piglets, growing pigs, and sows); poultry such as turkeys and chicken (including but not limited to broiler chicks, layers); and fish.

The term "feed" or "feedstuff" or "feed ingredient" or "feed product" means any compound, grain, nut, forage, silage, preparation, mixture, or composition suitable for, or intended for intake by an animal.

The term "forage" means plant material (mainly plant leaves and stems) eaten by grazing animals.

The term "silage" means a fermented, high-moisture stored fodder which can be fed to ruminants.

Preferably, the feed is a grain and forage or silage based product. More preferably the feed ingredients comprise cereal(s), e.g., one or more of corn (maize), wheat, barley, rye, rice, sorghum and millet.

In one embodiment, the feed ingredient may be derived solely from cereal(s), and in another embodiment partly from legumes (e.g., soybean), partly from cereals and partly from animal products. The grain based feed may comprise whole or milled grain (e.g., wet or dry milled grain), including grain based product comprising fractions of wet or dry milled grain (e.g., gluten, protein, starch, and/or oil fractions). Also included are feed ingredients comprising by-product from brewing and/or fermentation processes (e.g., spent grains). Spent grains are the by-products from the production of alcoholic beverages and ethanol fuels. Brewers' spent grain (BSG) is the residue of beer making in breweries, which use malted barley as the major raw material. Distiller's' spent grain (DSG) is the product left in distilleries after alcohol is removed by distillation from the fermented grains such as corn, wheat, barley, rice, and rye. Distiller's' spent grain is also known as distiller's grain. Wet distiller's grain (WDG) is dried to produce dried distiller's grain (DDG) which is used primarily as animal feed.

In another embodiment, the present invention provides a composition comprising mycotoxin-deactivating aptamers and one or more mycotoxin-adsorbing/binding agents including, but not limited to, sodium bentonite, calcium bentonite, smectite sepiolite, sodium calcium montmorillonite, organophil modified montmorillonite, modified montmorillonite nanocomposite, wyoming sodium montmorillonite, zeolites (clinoptilolite, calcium/potassium/sodium hydrated aluminosilicate), hydrated sodium calcium aluminosilicate (HSCAS), activated carbon, superactivated charcoal, yeast cell wall extracts/fractions (e.g., polymeric glucomannan, esterified glucomannan, beta-glucans fraction or dry yeast cell wall fraction), micronized fibers, polymers (cholestyramine & polyvinylpolypyrrolidone), activated diatomaceous earth, plant fibres, complexed hydrated aluminium silicate, kaolinite, feldspartz, quartz, carbonaceous material, and hydrated sodium-potassium-calcium aluminosilicate.

In yet another embodiment, the present invention provides a composition comprising mycotoxin-deactivating aptamers and one or more mycotoxin-detoxifying biotransforming agents including, but not limited to, *Eubacterium* sp. BBSH 797, *Nocardia asteroids, Mycobacterium fluoranthenivorans* sp., *Rhodococcus erythropolis, Alcaligenes* species., *Bacillus* species., *Achromobacter* species., *Flavobacterium* species, *Pseudomonas* species, *Lactobacillus rhamnosus* train GG, *Lactobacillus helveticus* 46 & 72, *Lactobacillus casei, Lactobacillus lactis, Streptococcus thermophilus* C5 and NG40Z, *Lactobacillus paraplantarum, Stenotrophomonas maltophila, Saccharomyces cerevisiae, Cupriavidus basilensis* OR16 *Aspergillus niger, Eurotium herbariorum, Rhizopus* species, *Trichosporon mycotoxinivorans, Phaffia rhodozyma*, and *Xanthophyllomyces dendrorhous.*

In other embodiment, the present invention provides a composition comprising mycotoxin-deactivating aptamers and one or more mycotoxin degrading and detoxifying enzymes including, but not limited to, protease A, pancreatin, carboxypeptidase A, epoxidase from *Eubacterium*, lactonohydrolase, catalase, dehydrogenase, laccase, xylanase, esterase, lipase, oxidase, amino acid oxidase, peroxidase, lactoperoxidase, manganese peroxidase, polysaccharase and dehydrogenase.

In a further embodiment, the present invention provides a composition comprising a mycotoxin-deactivating aptamers and one or more mycotoxin toxicity-reducing antioxidants in humans and animals. These antioxidants include, but not limited to, rutin, quercetin, lutein, lecithin, melatonin, mannitol, curcumin, curcuminoids, lycopene, allyl sulfides, fructose, chlorophyll and derivatives, sodium thiosulfate, glutathione, methionine, aspartame, trace elements (selenium, zinc, magnesium), catechin (epigallocatechin gallate, epicatechin gallate), morin, kaempferol, fisetin, naringin, vitamins (vitamins E, C, A, B), coenzyme Q10, provitamins (carotene and carotenoids), eugenol, vanillin, caffeic acid, and cholinergic acid.

In yet a further embodiment, the present invention provides the mycotoxins of significant importance to food and feed safety, human healthcare, and to livestock industry. The mycotoxins against which aptamers can be developed include, but not limited to, aflatoxins (AFB1, AFB2, AFG1, AFG1, AFG2, AFM1), ochratoxin A, citrinin, citreoviridin, cyclopiazonic acid, moniliformin, penitrem A, PR toxin, sterigmatocystin, rubratoxin, deoxynivalenol, nivalenol, 3-acetyl deoxynivalenol, 15-acetyl deoxynivalenol, diacetoxyscirpenol, Fuserenon-X, T-2, HT-2, T-2 tetraol, neosolaniol, fumonisins, (FB1, FB2, FB3), ergot alkaloids (e.g., ergotamine), tremorgens, zearalenone, and alterneriol To achieve the foregoing and in accordance with the purposes of the present invention as described herein, a novel method is described for deactivating mycotoxins present in animal feeds. In particular, in a preferred embodiment, the invention provides a method and a composition for deactivating mycotoxins present in animal diets containing specific mycotoxin-deactivating aptamers alone or in combination with one or more adsorbing and biotransforming agents. The mycotoxin-specific aptamers are produced based on SELEX technology using a library of random oligonucleotide (e.g. DNA) sequences the ones with the best affinity for the target mycotoxin are selected through series of cycles with increasing stringency conditions.

Aptamers are oligonucleotide (single-stranded DNA or RNA or peptide molecules that bind to specific targets with high affinity. The advent of aptamers was propelled by the discovery of "Systematic Evolution of Ligands by Exponential enrichment" or SELEX [Tuerk, C. and Gold, L. Science. 1990; 249: 505-510; Ellington, A. D. and Szostak, J. W. Nature. 1990; 346: 818-822) and related combinatorial methods of in vitro selection. In SELEX, large populations of oligonucleotides (typically ~$10^{14}$ molecules of up to 100 nucleotides in length) are screened for their potential binding affinity for a defined target. In this chemical process, the initial population of oligonucleotides is bound to the selected target and only the species capable of binding are retained, PCR-amplified, and used for subsequent rounds of selection [Sun, H. and Zu, Y. A. Molecules. 2015; 20: 11959-11980). By modulating various parameters of the selection experiment, including the nature of the target, the length of the randomized region of the original library, and the selection stringency, a broad array of multifunctional aptamers can be obtained. Moreover, since the inception of the traditional SELEX method in 1990, numerous modifications and variants have been developed to fit the choice of the target, the different conditions, and include new technologies such as high-throughput sequencing methods and microfluidics [Ozer, A. et al. Mol. Ther. Nucleic Acids. 2014; 3, e183; Darmostuk, M. et al. Biotechnol. Adv. 2015; 33].

Modified aptamers can be obtained either (1) by introducing modifications into the scaffold of selected aptamers via standard solid-phase synthesis or (2) by using modified nucleoside triphosphates (dN*TPs and N*TPs) directly in the selection process [Tolle, F. and Mayer, G. Chem. Sci. 2013; 4: 60-67; Jellinek, D. et al., Biochemistry. 1995; Pagratis, N. C. et al., Nat. Biotechnol. 1997; 15: 68-73; Kuwahara, M. and Sugimoto, N. Molecules. 2010; 15: 5423-5444].

The key advantages of aptamers vs. antibodies include: (i) in vitro development which obviates host animals, (ii) ability to develop aptamers against native toxins without toxoid production, (iii) greater reproducibility of aptamers from batch-to-batch due to chemical synthesis, (iv) more rapid development of neutralizing agents by robotic means against multidrug resistant bacteria or lethal viruses, (v) unlimited inexpensive production of DNA aptamers at the gram or greater scale by PCR or asymmetric PCR (predominantly single-stranded PCR products), (vi) ability to store lyophilized aptamers indefinitely and obviate cold storage, (vii) reusability; aptamers can be heat-denatured, cooled to re-conform and used for many rounds of analyte binding and detection, and (viii) little or no immunogenicity.

Modifications located at the level of the sugar unit, the nucleobase, or the backbone of the constituting nucleotides can be introduced using dN*TPs as vectors in selection experiments. However, for dN*TPs to be acceptable candidates in SELEX, they obligatorily must be good substrates for polymerases, and the resulting modified sequences need to serve as templates for the conversion into wild-type DNA under PCR conditions (Keefe, A. D. and Cload, S. T. Curr. Opin. Chem. Biol. 2008; 12: 448-456; Hipolito, C. J. Org. Biomol. Chem. 2011; 9: 2266-2273).

Recent advances in protein engineering and the development of the compartmentalized self-replication (CSR) and compartmentalized self-tagging (CST) strategies have allowed for the evolution of numerous polymerases with expanded substrate tolerance (Kranaster, R. and Marx, A. ChemBioChem. 2010; 11: 2077-2084). Therefore, finding conditions for the successful polymerization of particular (d)N*TPs can readily be achieved by assessing the substrate acceptance using a pool of engineered and/or evolved polymerases. The nature of the functionalities appended on the nucleoside tri-phosphates along with their use in SELEX includes, but not limited to, the following: (i) sugar modifications focusing mostly on the 2'-position of the deoxyribose sugar unit (e.g. 2'fluoro pyrimidines); (ii) nucleoside triphosphate backbone modifications; (iii) modifications of the nucleobases that are mostly located at the C5-position of the pyrimidines and the N7 of 7-deaza-purines; (iv) SOMAmers (Slow Off-rate Modified Aptamers) and were shown to tightly and specifically bind to their targets; and (v) using L-nucleosides to foster mirror-image aptamers called ‘Spiegelmers”.

Aptamers have applications in developing diagnostics, diagnostic assays (e.g., Enzyme-Linked Aptamer Sorbent Assay or ELASA), antimicrobials against bacteria, protozoa & viruses, therapeutics, drug delivery system, and in neutralizing toxins and venoms (Bruno, J. G., Molecules. 2015; 20:6866-6887). US Pat. 2006/0121489 describes the use of aptamers for screening, including high-throughput screening and kits, of target bioterror agents, such as *Bacillus, Yersinia, Francisella, Vibrio, Brucella* and *Clostridium*. Furthermore, the bioterror agents may include a flavivirus, a hepadnavirus, a coronavirus, a hanta virus, a smallpox virus, a hemorrhagic fever virus, and/or a neuropathologic virus. Additionally, toxins or their subunits for determination may be Aflatoxins, Botulinum toxins, *Clostridium* toxins, Conotoxins, Ricins, Saxitoxins, Shiga toxins, Staphylococcusaureus toxins, Tetrodotoxins, Verotoxins, Microcystins (Cyanginosin), Abrins, Cholera toxins, Tetanus toxins, Trichothecene mycotoxins, Streptococcal toxins, *Pseudomonas* A toxins, Diphtheria toxins, *Listeria monocytogenes* toxins, *Bacillus anthracis* toxic complexes, *Francisella tularensis* toxins, whooping cough pertussis toxins, *Yersinia pestis* toxic complexes, *Yersinia enterocolytica* enterotoxins, *Brucella* toxins, and *Pasteurella* toxins, or mixtures thereof.

Despite the great promise of nucleic acid aptamers in the areas of diagnostics and therapeutics for their lack of immunogenicity and other desirable properties, few truly successful aptamer-based products exist in the clinical or other markets. Core deficiencies probably stem from industrial commitment to antibodies including a huge financial investment in humanized monoclonal antibodies and a general ignorance about aptamers and their performance among the research and development community (Bruno, J. G., Molecules. 2015; 20:6866-6887). However, the key advantages of aptamers over antibodies, coupled with niche market needs that only aptamers can fill and more and more recent published data still point to a bright commercial future for aptamers.

Recent developments in aptamer-based therapeutics have been rewarded in the form of the first aptamer-based drug approved by the FDA to treat age-related macular degeneration (AMD), called Macugen offered by OSI Pharmaceuticals. In addition, the aptamer-based therapeutics are currently undergoing clinical trials for treating diseases such as Acute Coronary Syndrome, Hemophilia, Intravascular Thrombus, Acute Myeloid Leukemia, Renal Cell Carcinoma, Non-Small Cell Lung Cancer, and Diabetes Mellitus (Sundaram, P. Eur. J. Pharm. Sci. 2013; 48: 259-271). A number of researchers and companies have tried to push aptamers into environmental niche markets and food safety testing with some very sensitive and specific assays for the major food-borne bacterial pathogens, viruses, food-borne toxins, antibiotics and pesticides (Kamaya-Gonzalez, A. et al., Sensors. 2013; 13: 16292-16311; Wang, L. et al. Biotechnol Lett. 2012; DOI: 10.1007/s10529-012-0850-6) Ultrasensitive aptamer-coated magnetic bead concentrating methods to probe foods for rare pathogens or viruses coupled to PCR detection assays or fluorescence detection have been shown to cut hours, if not days, off of culture enrichment and reporting times (Ka Lok Hong and L. J. Sooter, Biomed. Res. International. 2015; pp. 1-39; Davydova, A. et al. Crit. Rev. Microbiol. 2015; DOI: 10.3109/1040841X.2015.1070115). Yet, no one has marketed an AOAC-approved aptamer-based food-borne pathogen test to date. However, some success has already been realized by NeoVentures Biotechnologies, Inc. (London, ON, Canada), which markets aptamer-based concentrating and purifying columns and assay kits for mycotoxins such as Ochratoxin A and Aflatoxins in corn, wheat, beer and wine.

Aptamer-based assays have been developed for detection of Aflatoxin B1/M1, Ochratoxin A, Zearalenone, T2-Toxin (Ka Lok Hong and L. J. Sooter, Biomed. Res. International. 2015; pp. 1-39; Won-Bo, S. Food Control. 2014; 36: 30-35; Guo, X. et al. Biosens. Bioelectron. 2014; 56:340-344; Rhouati, A. et al. Toxins. 2013; 5: 1988-2008; Chen, X. et al. Anal. Bioanal. Chem. 2013; 405:6573-6581; Chen, X. et al. J. Agric. Food Chem. 62: 10368-10374), and Fumonisin B1 (McKeague, et al., Int. J. Mol. Sci. 2010; 11: 4864-4881). To date, several highly specific aptamers have been developed against a variety of bacterial toxins (e.g. *Shigella* toxins, *Clostridium* toxins & *Staphylococcus aureus* $\alpha$-toxin) and snake venoms to neutralize them (Bruno, J. G. Molecules. 2015; 20: 6866-6887; US Pat. Pub. No. 2004/0023265; US Pat. Pub. No. 2012/0231467; Vivekananda, J. et al. Biochem. Biophys. Res. Commun. 2014; 433-438). These toxic compounds would all require neutralization by a cocktail of "polyclonal' aptamers to be effective as a single anti-venom product. Any aptamer that binds to a toxin or venom component specifically can possibly be converted into a DNAzyme or aptazyme with molecular engineering. Enzymatic aptamers would reduce the requisite antidote dose.

Although there are reports on the potential applications of aptamers in developing analytical assays for bacterial and fungal toxins (mycotoxins), and in neutralizing bacterial toxins and snake venoms, none of the above references describes the use of aptamers for neutralizing or deactivating or detoxifying mycotoxins. An aptamer-mycotoxin complex can not only deactivate the toxic effects of mycotoxins when added to the feed but would also prevent the absorption of toxin in the feed from being absorbed in the gastrointestinal tract. As a result, the toxin will be excreted in the feces in a complexed non-toxic form. Furthermore, the new aptamer-based mycotoxin deactivator will be specific, and cost effective to use.

The mycotoxin-deactivating aptamers alone or compositions comprising mycotoxin-deactivating aptamers, mycotoxin-adsorbing agents and mycotoxin-biotransforming agents and mycotoxin toxicity-reducing agents provided by the present invention can be added to any commercially available feed or feedstuffs for livestock or companion animals including, but not limited to, premixes, concentrates and pelleted concentrates. The said aptamers alone or a composition provided by the present invention may be incorporated directly into commercially available mashed and pelleted feeds or fed supplementary to commercially available feeds. When incorporated directly into animal feeds, the present invention may be added to such feeds in amounts ranging from, but not limited to, 0.1 to about 10 kilograms (kegs) per tonne of feed. Preferably, when incorporated directly into animal feeds, the present invention may be added to such feeds in amounts ranging from, but not limited to, 0.3 to about 6 kgs per tonne of feed. In an especially preferred mycotoxin-deactivating aptamers alone or a composition comprising mycotoxin-deactivating aptamers, binding agents and biotransforming agents of the invention is added to feeds in amounts ranging from, but not limited to, about 1 to 3 kgs per tonne of feed. The aptamers alone or a composition contained in the present invention may be fed to any animal, including but not limited to, avian, bovine, porcine, equine, ovine, caprine, canine, and feline species. Furthermore, the proposed methods of deactivating of an extended range of mycotoxins are especially useful for alleviating the effect of mycotoxin concentration while fermenting grains during ethanol and beer fermentations. The resulting wet distiller's grain and dried distiller's grain, including DDGS, has on average a 3-fold increase in mycotoxin content compared to initial materials.

The compositions of the present invention may be added to mycotoxin-contaminated animal feed in amounts from, but not limited to, about 0.01% to 2% by weight of feed. In a preferred embodiment, the composition is added to mycotoxin-contaminated animal feed in amounts from, but not limited to, about 0.03% to 0.5% by weight of feed. In an especially preferred embodiment, the invention is added to mycotoxin-contaminated animal feed in amounts from, but not limited to, about 0.1% to 0.3% by weight of feed. Alternatively, the antibodies alone or a composition contained in the present invention may be directly fed to animals as a supplement in amounts ranging from, but not limited to, 0.01 to 200 grams per animal per day. An especially preferred embodiment comprises feeding the compositions of the present invention to animals in amounts ranging from, but not limited to, 0.1 to 30 grams per animal per day, depending on the animal species, size and feed intake of the animal, and the type of feed to which the composition is to be added. The mycotoxin-deactivating aptamer binds with its increased mycotoxin binding affinity and its ability to prevent or significantly decrease gastro-intestinal absorption or uptake of mycotoxins will improve animal performance and health, and reduce the incidence of mycotoxin-associated syndromes or diseases in affected animals when fed alone or in combination with other adsorbing and biotransforming agents.

Example 1: Indirect Enzyme-Linked Immunosorbent Assays for Mycotoxins

Indirect competitive ELISAs were developed for quantitation of the mycotoxins following the procedure outlined by Xiao et al. (J. Agric. Food Chem. 1995; 43: 2092-2097) and Li et al. (J. Food Prot. 11:952-1037, 1994). An example of an assay for mycotoxin is given below. The procedure for coating and blocking the microtiter plate with the aminodex AFB1 conjugate is similar to that used for the antibody titer assay. The following are then added to the appropriate microtiter plate wells: 75 µl of pH 7.2 PBS-T, 10 µl of AFB1 or AFB1 standard diluted with methanol, and 65 µl of chicken anti-AFB1 antibodies diluted in pH 7.0 PBS-T. The plates are incubated at 37° C. for 1 h. The remaining procedure is the same as for antibody titer assay. The antibody titer assays for the other anti-mycotoxin antibodies are similar to those for the AFB1 antibody.

Example 2: Production of Aflatoxin B1 Specific Aptamers

The production of aptamers was mostly based on SELEX (Systematic Evolution of Ligands by Exponential Enrichment) technology. Briefly, from a library of random sequences the one/ones with the best affinity for the target molecule were selected through a series of cycles with increasing stringency conditions. This SELEX approach was based on the Morse protocol (Morse, D. P. Biochem. Biophys. Res. Commun. 2007; 359: 94-101), modified to be applied to DNA sequences, and one of the target molecules is AFB1. The procedure involved the following steps: (i) An initial library of random sequences was digested to obtain single strand DNA pool for the selection; (ii) The single strand DNA sequences were put on magnetic beads through hybridization with a short oligonucleotide immobilized on the surface; (iii) Upon incubation with the target, i.e. AFB1, aptamers that undergo a conformational change due to the interaction with the target were displaced from the beads are collected; and (iv) The selected aptamers were amplified by PCR and used as starting material for the following cycle. To monitor the SELEX process, during step (iii) a negative control was performed by incubating the beads in absence of AFB1. The difference in yield between positive and negative control is assessed by semi-quantitative PCR. To evaluate the outcome of the SELEX, the Surface Plasmon Resonance (SPR) was used. By immobilizing the investigated cycle on one cell and the starting library in the reference cell, there was an increase in the differential signal. The cycle 12 library was sent to sequencing. After sequence analysis, some aptamer candidates were tested singularly on SPR to check the most performing ones, which can be used as probe molecules in application. The molar binding capacity of the aptamer for AFB1 was determined using an ELASA (the substitution of an antibody in an ELISA with an aptamer; Toh, et al. Biosens. Bioelectronic. 2015; 64: 392-403).

Example 3: Aflatoxin B1 (AFB1) Lethality Test in Zebrafish

The goal of this study was to determine the dose-dependent aflatoxin B1 (AFB1) toxicity induced lethality in Zebrafish.

Materials & Methods:

Zebrafish embryos were generated by using a Mass Embryo Production System. Approximately 50 embryos were generated per female zebrafish. Embryos were cleaned by removing dead embryos and sorted by developmental stage. As embryos receive nourishment from an attached yolk sac, no feeding was required for 6-days post fertilization (dpf). Aflatoxin B1 was supplied by Cayman Chemical Company (Ann Arbor, Mich., USA). In this pilot study, the Maximum Tolerable Concentration (MTC) of AFB1 was determined. 2 dpf zebrafish were distributed into 6-well plates containing 4 ml fish water/well; 4 μl sub-MS solution of AFB1 was then added directly to fish water. Zebrafish were exposed to AFB1 continuously for 72 hr. Untreated and 0.1% DMSO-treated zebrafish were used as controls for the lethality test. Dimethyl sulfoxide (DMSO) can help transport small molecules through the skin. A lethality test was performed using 0, 0.25, 0.5 and 1 μM for AFB1; 30 zebrafish were used for each condition. To confirm that vehicle had no effect on lethality, treatment with 0.1% DMSO was compared with untreated zebrafish. Dead zebrafish were counted and removed daily; after 72 hr treatment, total lethality was calculated. To obtain mean and standard deviation (SD) for each condition, experiments were performed 3 times.

Results:

There was no lethality after 72 hr incubation for zebrafish incubated in fish water or fish water plus 0.1% DMSO (Controls). The average percent mortalities for zebrafish treated with 0.25, 0.5 and 1.0 μM AFB1 in 0.1% DMSO were 0, 71.1, 100 and 100%, respectively (Table 1).

TABLE 1

Results of AFB1 Toxicity Induced Lethality Test in Zebrafish[1]

| | % Lethality | | | | |
|---|---|---|---|---|---|
| Final Conc. (μM) | Exp. 1 | Exp. 2 | Exp. 3 | Mean | SD |
| Untreated (No DMSO) | 0 (0/30) | 0 (0/30) | 0 (0/30) | 0 (0/30) | 0.0 |
| 0 + 0.1% DMSO | 0 (0/30) | 0 (0/30) | 0 (0/30) | 0 (0/30) | 0.0 |
| 0.25 + 0.1% DMSO | 73.3 (22/30) | 86.7 (26/30) | 53.3 (0/30 | 71.1 (21/30) | 16.8 (5/30) |
| 0.5 + 0.1% DMSO | 100 (30/30) | 100 (30/30) | 100 (30/30) | 100 (30/30) | 0.0 |
| 1 + 0.1% DMSO | 100 (30/30) | 100 (30/30) | 100 (30/30) | 100 (30/30) | 0.0 |

[1]Numbers in Parentheses: Number of dead zebrafish divided by number of zebrafish used per well

Example 4: Evaluation of Neutralizing Effect of Aflatoxin B1 (AFB1)-Specific Aptamer (Apt) on AFB1 Toxicity Induced Lethality in Zebrafish (ZF)

The goal of this study was to assess the neutralizing effect of aflatoxin B1 (AFB1) specific aptamer on AFB1 toxicity induced lethality in zebrafish.

Materials & Methods:

Zebrafish embryos were generated by using a Mass Embryo Production System. Approximately 50 embryos were generated per female zebrafish. Embryos were cleaned by removing dead embryos and sorted by developmental stage. As embryos receive nourishment from an attached yolk sac, no feeding was required for 6-days post fertilization (dpf). Aflatoxin B1 was supplied by Cayman Chemical Company (Ann Arbor, Mich., USA). 1 mg of AFB1 powder was dissolved in 3.18 ml of DMSO to prepare a 1.0 mM Master Stock (MS) solution. A 0.25 mM sub-MS was then prepared Aflatoxin B1 specific aptamer [Sequence of SEQ ID NO. 1: 5'-GTT GGG CAC GTG TTG TCT CTC TGT GTC TCG TGC CCT TCG CTA GGC CCA CA/3InvdT/-3'] (CN 104964969) was purchased from NeoVentures Biotechnology (London, ON, Canada). Aflatoxin B1 specific aptamer Master Stock (MS) solution was prepared by dissolving a known quantity (~350 nmoles) of aptamer powder in 2.8 ml fish water to generate a 125 μM AFB1-aptamer MS. 40 μl of 125 μM AFB1-aptamer MS solution was pre-incubated with 4 μl of 0.25 mM AFB1 in 6-well microplates containing 1956 μl fish water/well for 15 min. To ensure 4 ml final volume, after pre-incubation, 2 ml fish water containing 2 dpf self-hatched zebrafish (N=30) was added (Final conc. of AFB1-aptamer was 1.25 μM, 5 fold higher than final AFB1 conc). 2 dpf zebrafish were treated continuously with each condition for 96 hr. Final treatment conditions for 4 ml fish water are shown in Table 2. Final DMSO concentration was 1% for each condition.

TABLE 2

| Final Conditions for AFB1Toxicity Induced Lethality Test[1] | | |
|---|---|---|
| Condition | Final Conc. of AFB1 (μM) | Final conc. of AFB1-Aptamer (μM) |
| 0.1% DMSO | 0 | 0 |
| AFB1-Aptamer + 0.1% DMSO | 0 | 1.25 |
| AFB1 + 0.1% DMSO | 0.25 | 0 |
| AFB1 + AFB1-Aptamer + 0.1% DMSO | 0.25 | 1.25 |

[1]Dead zebrafish were counted daily and removed. After treatment for 96 hr, total lethality was calculated. To obtain mean and Standard Deviation (SD) for each condition, experiments were performed 3 times.

Figure 2:
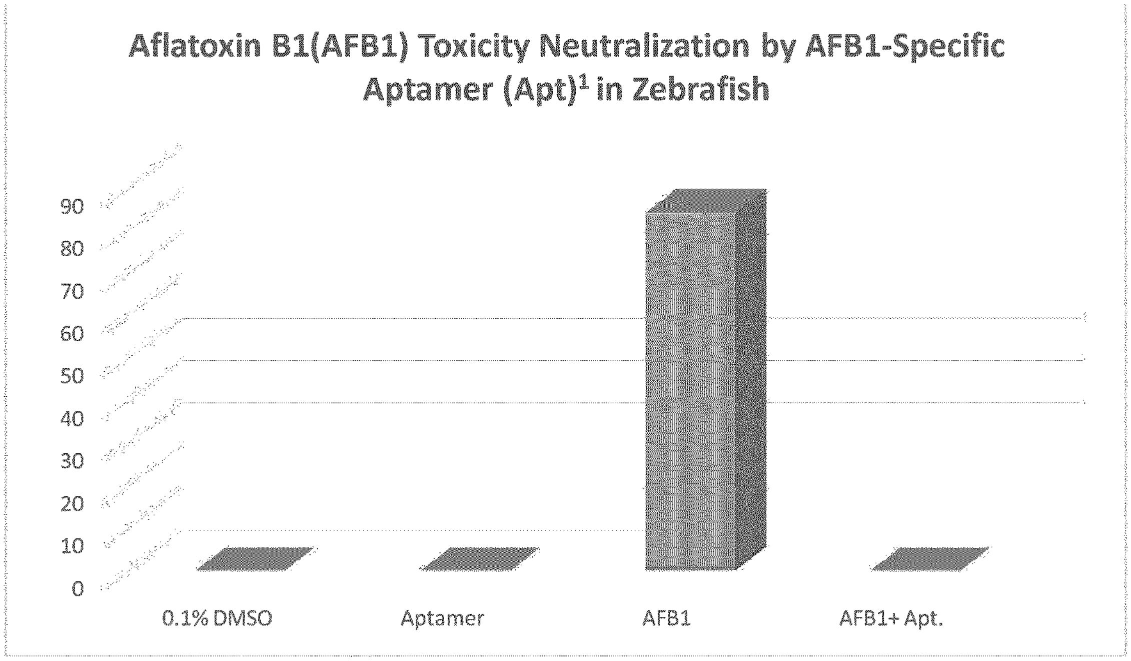
FIG. 2 shows the neutralizing effect of aflatoxin B1 (AFB1)-specific aptamer on AFB1 toxicity induced lethality in zebrafish.

Results:

After treatment for 96 hrs, 0% lethality was observed after treatment with 0.1% DMSO, validating the assay. 0% lethality was also observed after treatment with AFB1-specific aptamer alone+0.1% DMSO confirming that AFB1-specific aptamer did not induce lethality in zebrafish. However, 82.2±1.9% lethality was observed in zebrafish after treatment with AFB1 alone+0.1%. In contrast, 0% lethality was observed after treatment with AFB1 and AFB1-specific aptamer combination (AFB1+AFB1-Specific Aptamer; FIG. 1)+0.1% DMSO, indicating that AFB1-specific aptamer neutralized 100% AFB1 toxicity induced lethality in zebrafish (Table 3, FIG. 2).

TABLE 3

| Results of Testing the Neutralizing Effect Aflatoxin B1 (AFB1) Aptamer on AFB1 Toxicity Induced Lethality in Zebrafish[1] % Lethality | | | | | |
|---|---|---|---|---|---|
| Final Conc. (μM) | Exp. 1 | Exp. 2 | Exp. 3 | Mean | SD |
| 0.1% DMSO | 0 (0/30) | 0 (0/30) | 0 (0/30) | 0 | 0 |
| AFB1-Aptamer + 0.1% DMSO | 0 (0/30) | 0 (0/30) | 0 (0/30) | 0 | 0 |
| AFB1 + 0.1% DMSO | 80 (24/30) | 83.3 (25/30) | 83.3 (25/30) | 82.2 | 1.9 |
| AFB1 + AFB1-Aptamer + 0.1% DMSO | 0 (0/30) | 0 (0/30) | 0 (0/30) | 0 | 0 |

[1]Numbers in Parentheses: Number of dead zebrafish divided by number of zebrafish per well.

We claim:

1. A use of a composition comprising a mycotoxin-deactivating aptamer for inhibiting the toxicity of mycotoxins in animal feed, the use comprising mixing of the composition with a feed.

2. The use as claimed in claim 1, said composition further comprising one or more of: a mycotoxin-specific antibody, a mycotoxin-adsorbing agent, a mycotoxin-biotransforming agent, a mycotoxin-degrading enzyme and a mycotoxin toxicity-reducing antioxidant.

3. The use according to claim 1, wherein the aptamers are either individual mycotoxin-specific single stranded DNA (ssDNA) or single stranded RNA (ssRNA) molecules.

4. The use according to claim 1, wherein the composition is capable of detoxifying a wide spectrum of mycotoxins, including those selected from the group consisting of aflatoxins, deoxynivalenol, nivalenol, T-2 toxin, zearalenone, fumonisins, ochratoxin A, citrinin and ergotamine.

5. The use according to claim 1, wherein the mycotoxin-deactivating aptamer is AFB1-specific aptamer.

6. The use according to claim 1, wherein the mycotoxin-deactivating aptamer is at a concentration ranging from about 0.01% to about 2% by weight of the animal's daily feed ration.

7. The use according to claim 1, wherein the aptamer is at a concentration ranging from about 0.1% to about 0.3% by weight of the animal's daily feed ration.

8. The use according to claim 1, wherein the ingredients of feed are selected from the group consisting of corn, wheat, barley, rye, rice, sorghum, soybean, peanut, millet, brewers spent grain, distiller's spent grain, distiller's wet grain, and distiller's dried grain, forage and silage.

9. The use of claim 2, wherein the mycotoxin-adsorbing agent is selected from the group consisting of sodium bentonite, calcium bentonite, sodium-calcium montmorillonite, clinoptilolite, calcium/potassium/sodium hydrated aluminosilicate, hydrated sodium calcium aluminosilicate (HSCAS), activated carbon, dry yeast cells, polymeric glucomannan, esterified glucomannan and beta-glucan fractions of dry yeast cell wall, cholestyramine, polyvinylpolypyrrolidone, activated diatomaceous earth, plant fibres, kaolinite, and hydrated sodium-potassium-calcium aluminosilicate.

10. The use of claim 2, wherein the biotransforming agent is selected from the group consisting of *Eubacterium* sp. BBSH 797, *Nocardia asteroids, Mycobacterium fluoranthenivorans* sp., *Rhodococcus erythropolis, Alcaligenes* species., *Bacillus* species., *Achromobacter* species., *Flavobacterium* species, *Pseudomonas* species, *Lactobacillus rhamnosus* strain GG, *Lactobacillus helveticus* 46 & 72, *Lactobacillus casei, Lactobacillus lactis, Streptococcus thermophilus* C5 and NG40Z, *Lactobacillus paraplantarum, Stenotrophomonas maltophila, Saccharomyces cerevisiae, Cupriavidus basilensis* OR16 *Aspergillus niger, Eurotium herbariorum, Rhizopus* species., *Trichosporon mycotoxinivorans, Phaffia rhodozyma*, and *Xanthophyllomyces dendrorhous.*

11. The use of claim 2, wherein the mycotoxin-degrading enzyme is selected from the group consisting of protease A, pancreatin, carboxypeptidase, epoxidase from *Eubacterium*, lactonohydrolase, catalase, laccase, xylanase, esterase, lipase, oxidase, amino acid oxidase, peroxidase, lactanase, lactoperoxidase, lactonase, manganese peroxidase, polysaccharase and dehydrogenase.

12. The use of claim 2, wherein the mycotoxin toxicity-reducing antioxidant is selected from the group consisting of rutin, quercetin, lutein, lecithin, melatonin, curcumin, curcuminoids, allyl sulfides, chlorophyll and derivatives, sodium thiosulfate, glutathione, methionine, aspartame, selenium, zinc, catechin, vitamin E, vitamin C, vitamin A, vitamin B, coenzyme Q10, carotene and carotenoids.

13. The use of claim 1, wherein the composition comprises aptamers, egg-yolk antibodies and hydrated sodium calcium aluminosilicate (HSCAS).

14. The use of claim 1, wherein the composition comprises aptamers, hydrated sodium calcium aluminosilicate (HSCAS), activated carbon, cholestyramine, *Saccharomyces cerevisiae, Lactobacillus* species, *Eubacterium* sp. BBSH 797, epoxidase and rutin.

15. The use of claim 1, wherein the aptamer is specific to a mycotoxin selected from the group consisting of aflatoxin B1, deoxynivalenol, zearalenone, fumonisin B1 and ochratoxin A.

16. The use of claim 1, wherein the aptamer is produced using SELEX technology.

17. The use of claim 1, wherein the mycotoxin-deactivating aptamer is protected from nuclease degradation by aptamer modifications including changes on the 2'-position of the deoxy-ribose sugar unit in nucleoside triphosphate backbone and nucleobases located at the C5-position of the pyrimidines and the N7 of 7-deaza-purines.

18. The use according to claim 1, wherein the composition is aqueous.

19. The use according to claim 1, wherein the composition is a powder.

20. The use according to claim 4, wherein the aflatoxins comprise AFB1, AFB2, AFG1, AFG2.

* * * * *